US010347377B1

(12) United States Patent
Lavin

(10) Patent No.: US 10,347,377 B1
(45) Date of Patent: *Jul. 9, 2019

(54) WEB ENABLED AUDIOVISUAL MEDICATION DISPENSING

(71) Applicant: Omcare LLC., Burnsville, MN (US)

(72) Inventor: Lisa Lavin, Prior Lake, MN (US)

(73) Assignee: Omcare LLC., Burnsville, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/131,017

(22) Filed: Sep. 13, 2018

Related U.S. Application Data

(63) Continuation of application No. 14/931,837, filed on Nov. 3, 2015, now Pat. No. 10,078,732, which is a continuation of application No. 13/495,607, filed on Jun. 13, 2012, now Pat. No. 9,202,011.

(60) Provisional application No. 61/498,010, filed on Jun. 17, 2011.

(51) Int. Cl.
| | | |
|---|---|---|
| G06F 17/00 | (2019.01) | |
| B65D 83/04 | (2006.01) | |
| H01R 43/00 | (2006.01) | |
| G06F 19/00 | (2018.01) | |
| A61J 7/04 | (2006.01) | |
| G06Q 10/08 | (2012.01) | |
| G07F 11/00 | (2006.01) | |
| A61J 7/00 | (2006.01) | |
| A61J 1/03 | (2006.01) | |
| G16H 30/20 | (2018.01) | |
| G07F 17/00 | (2006.01) | |
| G16H 40/67 | (2018.01) | |

(52) U.S. Cl.
CPC ............ *G16H 30/20* (2018.01); *A61J 7/0084* (2013.01); *G06F 19/00* (2013.01); *G06Q 10/087* (2013.01); *G07F 11/002* (2013.01); *G07F 17/0092* (2013.01); *G16H 40/67* (2018.01); *A61J 7/0418* (2015.05); *A61J 2200/30* (2013.01); *A61J 2205/70* (2013.01); *Y10T 29/53087* (2015.01)

(58) Field of Classification Search
CPC ... A61J 7/0076; A61J 7/0084; G06F 19/3462; Y10T 29/53087; G07F 11/002; G07F 17/0092
USPC ........................................ 700/236, 240, 244
See application file for complete search history.

(56) References Cited

U.S. PATENT DOCUMENTS

| | | |
|---|---|---|
| 3,732,544 A | 5/1973 | Obland |
| 4,360,125 A | 11/1982 | Martindale et al. |
| 4,616,316 A | 10/1986 | Hanpeter et al. |
| 4,653,009 A | 3/1987 | Brown |
| 4,695,954 A | 9/1987 | Rose et al. |
| 5,630,347 A | 5/1997 | Elvio |
| 5,646,912 A | 7/1997 | Cousin |
| 5,713,485 A | 2/1998 | Liff et al. |
| 5,945,651 A | 8/1999 | Chorosinski et al. |
| 6,004,020 A | 12/1999 | Bartur |
| 6,263,259 B1 | 7/2001 | Bartur |

(Continued)

*Primary Examiner* — Michael Collins
(74) *Attorney, Agent, or Firm* — Albert W. Watkins

(57) ABSTRACT

The disclosure relates generally to methods and devices for taking care of elderly, disabled, or other dependents. The devices and methods may be useful for dependents that are not willing or able to live in an environment which has a caretaker physically present. Example devices and methods can facilitate communication between a caretaker and a dependent. Devices and methods can optionally facilitate disbursing medications remotely.

18 Claims, 4 Drawing Sheets

(56) References Cited

U.S. PATENT DOCUMENTS

| | | |
|---|---|---|
| 6,394,306 B1 | 5/2002 | Pawlo et al. |
| 6,415,202 B1 | 7/2002 | Halfacre |
| 6,527,138 B2 | 3/2003 | Pawlo et al. |
| 6,529,801 B1 | 3/2003 | Rosenblum |
| 6,539,281 B2 | 3/2003 | Wan et al. |
| 6,594,549 B2 | 7/2003 | Siegel |
| 6,607,094 B2 | 8/2003 | MacDonald |
| 6,615,107 B2 | 9/2003 | Hubicki |
| 6,625,518 B2 | 9/2003 | Depeursinge |
| 6,697,704 B2 | 2/2004 | Rosenblum |
| 6,732,884 B2 | 5/2004 | Topliffe et al. |
| 6,766,218 B2 | 7/2004 | Rosenblum |
| 6,957,126 B2 | 10/2005 | Kim |
| 6,961,285 B2 | 11/2005 | Niemiec et al. |
| 7,155,202 B2 | 12/2006 | Helal |
| 7,264,136 B2 | 9/2007 | Willoughby et al. |
| 7,359,765 B2 | 4/2008 | Varvarelis et al. |
| 7,369,919 B2 | 5/2008 | Vonk et al. |
| 7,440,817 B2 | 10/2008 | Fu |
| 7,654,230 B2 | 2/2010 | Kroll |
| 7,711,449 B2 | 5/2010 | Abdulhay et al. |
| 7,801,745 B2 | 9/2010 | Walker et al. |
| 7,873,435 B2 | 1/2011 | Yuyama et al. |
| 7,878,152 B2 | 2/2011 | Kroll |
| 7,917,246 B2 | 3/2011 | Handfield et al. |
| 7,963,201 B2 | 6/2011 | Willoughby et al. |
| 7,991,507 B2 | 8/2011 | Liff et al. |
| 8,019,471 B2 | 9/2011 | Bogash et al. |
| 8,060,249 B2 | 11/2011 | Bear et al. |
| 8,175,746 B2 | 5/2012 | Godlewski |
| 8,196,774 B1 | 6/2012 | Clarke et al. |
| 8,201,522 B2 | 6/2012 | Kroll |
| 8,224,483 B1 | 7/2012 | Ansari et al. |
| 8,453,874 B2 | 6/2013 | Simpson et al. |
| 8,600,548 B2 | 12/2013 | Bossi et al. |
| 8,600,549 B2 | 12/2013 | Park |
| D699,758 S | 2/2014 | Lavin et al. |
| 8,757,435 B2 | 6/2014 | Van Oort et al. |
| 9,202,011 B2 * | 12/2015 | Lavin .................. G06F 19/3418 |
| 10,078,732 B2 * | 9/2018 | Lavin .................. G06F 19/3418 |
| 2001/0054071 A1 | 12/2001 | Loeb |
| 2002/0113077 A1 | 8/2002 | Topliffe et al. |
| 2002/0153411 A1 | 10/2002 | Wan et al. |
| 2005/0259641 A1 | 11/2005 | Beninato et al. |
| 2006/0161295 A1 | 7/2006 | Yun |
| 2006/0184271 A1 | 8/2006 | Loveless |
| 2006/0276931 A1 | 12/2006 | Walker et al. |
| 2008/0105588 A1 | 5/2008 | Tran et al. |
| 2009/0022293 A1 | 1/2009 | Routt |
| 2009/0105876 A1 | 4/2009 | Simpson et al. |
| 2009/0315702 A1 | 12/2009 | Cohen Alloro et al. |
| 2010/0026817 A1 | 2/2010 | Ryan et al. |
| 2010/0076595 A1 | 3/2010 | Nguyen |
| 2010/0152885 A1 | 6/2010 | Regan et al. |
| 2010/0164716 A1 | 7/2010 | Estevez et al. |
| 2010/0194976 A1 | 8/2010 | Smith et al. |
| 2010/0256808 A1 | 10/2010 | Hui |
| 2011/0068115 A1 | 3/2011 | Choi et al. |
| 2011/0080459 A1 | 4/2011 | Kroll |
| 2011/0115875 A1 | 5/2011 | Sadwick et al. |
| 2011/0202174 A1 | 8/2011 | Bogash et al. |
| 2012/0081225 A1 | 4/2012 | Waugh et al. |
| 2012/0083666 A1 | 4/2012 | Waugh et al. |
| 2012/0101630 A1 | 4/2012 | Daya et al. |
| 2012/0323360 A1 | 12/2012 | Lavin |
| 2014/0005826 A1 | 1/2014 | Apell et al. |
| 2016/0055318 A1 | 2/2016 | Lavin |

\* cited by examiner

WEB ENABLED AUDIOVISUAL MEDICATION DISPENSING

RELATED APPLICATION

This application is a continuation of U.S. Utility application Ser. No. 14/931,837 entitled "Web Enabled Audiovisual Medication Dispensing," filed with the United States Patent and Trademark Office on Nov. 3, 2015 and now granted as U.S. Pat. No. 10,078,732 on Sep. 18, 2018, which in turn is a continuation of U.S. Utility application Ser. No. 13/495,607 [entitled "Web Enabled Audiovisual Medication Dispensing,"] filed with the United States Patent and Trademark Office on Jun. 13, 2012 and now granted as U.S. Pat. No. 9,202,011 on Dec. 1, 2015, and claims the benefit of U.S. Provisional Application 61/498,010 (entitled "Web Enabled Audiovisual Medication Dispensing Apparatus," filed Jun. 17, 2011).

BACKGROUND

Medical care devices for delivery of medication to elderly, child, or disabled dependents may allow the dependents to remain in their homes longer, reduce costs of medical care, and provide a way for caretakers to ensure the delivery of the correct type and quantity of medications to their charges.

Communication with elderly or impaired persons may be more challenging than with other persons due to a lower rate of adoption of electronic communication. Some reasons for this lower rate of adoption may be impairments to vision, hearing, cognitive skills, or mobility. The physical effects of aging, such as arthritis and failing eyesight and memory, can cause issues in the autonomous taking of medicines.

SUMMARY

In certain examples, an apparatus for communicating with a dependent may comprise web link circuitry operable to communicate with a remote device, a medication cartridge assembly electrically coupled to the web link circuitry, and a mass-sensing receptacle electrically coupled to the web link circuitry.

In certain examples, a method of making an apparatus may include electrically coupling web link circuitry with a medication cartridge assembly, wherein the web link circuitry is operable to communicate with a remote device and electrically coupling the web link circuitry with a mass-sensing receptacle, wherein the mass-sensing receptacle is operable to detect if mass is present in the mass-sensing receptacle.

In certain examples, an apparatus may comprise web link circuitry, where the web link circuitry is operable to communicate with a smartphone of a caregiver, the web link circuitry is configured to allow only an authorized user to establish communication with the dependent. The apparatus may further comprise a medication cartridge assembly, wherein the medication cartridge assembly is electrically coupled to the web link circuitry. The apparatus may further comprise a mass-sensing receptacle, wherein the mass-sensing receptacle is electrically coupled to the web link circuitry, and wherein the mass-sensing receptacle is configured to transmit the mass of medication in the mass-sensing receptacle.

A BRIEF DESCRIPTION OF THE DRAWINGS

These as well as other objects and advantages of a web enabled audiovisual medication dispensing system will be more completely understood and appreciated by referring to the following more detailed description of the example embodiments of the disclosure in conjunction with the accompanying drawings of which:

Figure 1:
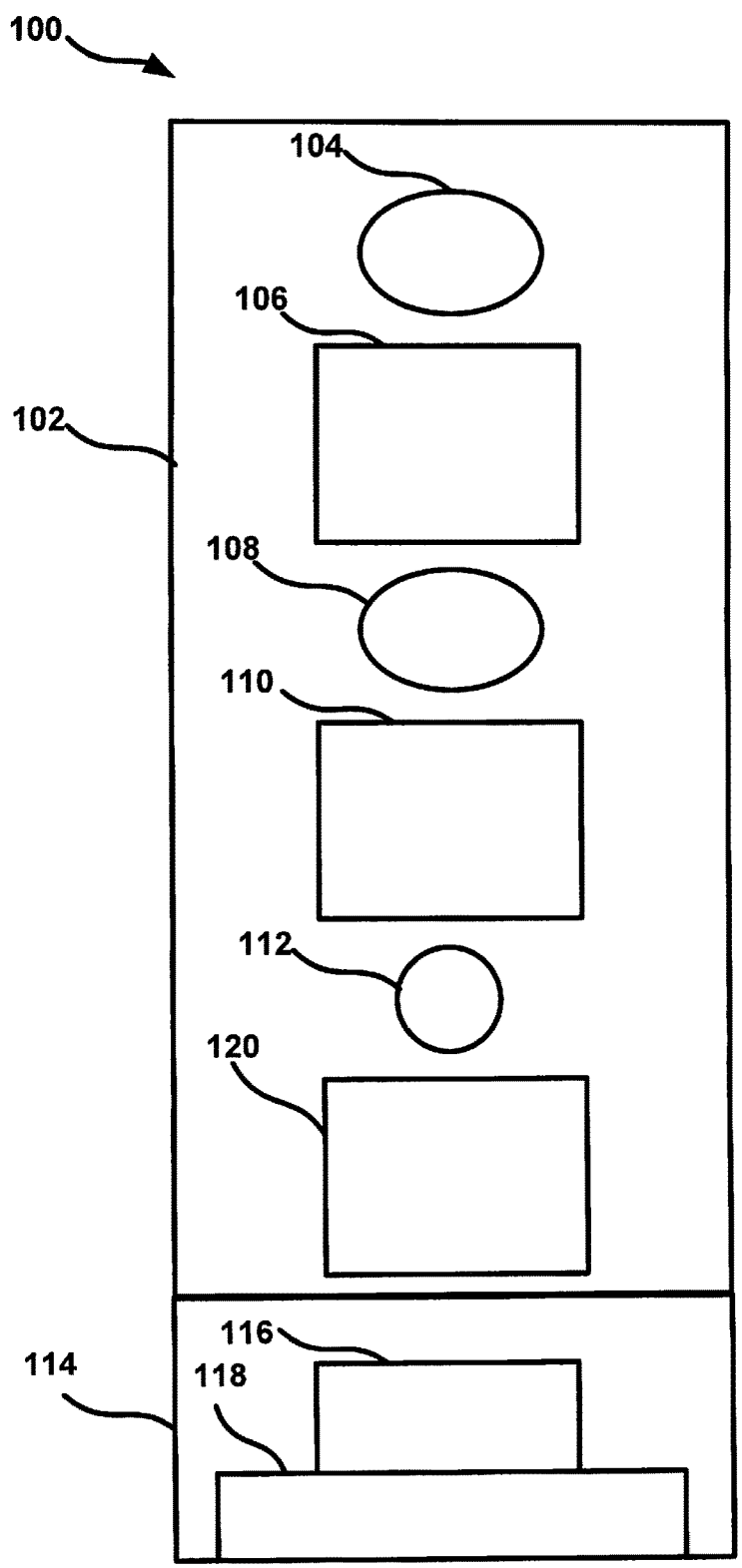
FIG. 1 is a front view illustration of an apparatus according to an example embodiment.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the disclosure is to cover all modifications, equivalents, and alternatives.

DETAILED DESCRIPTION

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical, and electrical changes may be made without departing from the scope of the present invention. The following description of example embodiments is, therefore, not to be taken in a limited sense, and the scope of the present invention is defined by the appended claims.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Devices and methods can facilitate communication with persons who may have trouble autonomously caring for themselves ("dependents"). Dependents may struggle with common communication technology, such as cellular phones, email, or text messaging. Certain example devices and methods can facilitate the provision of medication to dependents. Certain example devices and methods may combine both the ability to connect socially and the ability to provide remote medication management into a device that can be simple for a caregiver and the dependent to use. Certain embodiments of the devices and methods can allow a caretaker and dependent to communicate through a preconfigured VOIP (voice-over-internet-protocol software) connection, either via audio alone or via video call. Certain example devices and methods can facilitate the remote dispensing of medication by a caretaker. Certain embodiments of the device and its method of use can help ensure that the medication has been consumed.

Certain embodiments of the disclosure may be designed for use with elderly dependents. Elderly dependents often struggle with new technology, and the simplification of using voice-over-internet-protocol software (VOIP) technology may remove these barriers. Elderly dependents may need a caretaker due to deteriorating health, yet be unable or unwilling to move to an assisted living facility or hire a full-time caretaker. By providing access to a remote caretaker, devices or methods may help elderly dependents safely stay in their own homes longer.

Embodiments of the disclosure may be useful to intellectually disabled dependents. Intellectually disabled dependents similarly may struggle with modern communication technology, and simplification of technology, accomplished for example through the use of VOIP technology, may allow those dependents to more easily communicate with a remote caretaker.

Additionally, embodiments of the disclosure may be useful for child dependents. Children may lack the skills and maturity to communicate with a caretaker using modern communication technology, and simplification of technology accomplished, for example, through the use of VOIP technology, may allow those dependents to more easily communicate with a remote caretaker.

Many dependents have difficulty managing their own medication consumption. Even when medications are organized or prepackaged for the dependent, the dependent can forget to take the medication at the appropriate time. Certain embodiments of the disclosure may help dependent persons remember to take their medications.

FIG. 1 is a front view illustration of an apparatus 100 according to an example embodiment. The apparatus 100 may include a camera 104, a video display 106, a speaker 108, a one-touch call button 110, a microphone 112, and an optional keypad 120, arranged on or at least partially in, a communication housing 102. The camera 104, video display 106, speaker 108, one-touch call button 110, and microphone 112 may be arranged on, or at least partially in, the communication housing 102 such that a dependent can easily use the apparatus 100 to communicate with a caretaker. In certain examples, the medication dispensing apparatus 100 may include a medication management assembly 114. The medication management assembly 114 may include a medication door 116 and mass-sensing receptacle 118. The apparatus may be controlled by a computer control mechanism (not shown). In certain examples the computer control mechanism is a microcontroller, a motherboard, a processor, or other component capable of controlling electrically coupled components of the apparatus.

Certain examples may comprise a communication housing 102. The communication housing 102 may provide structure and protection for other components (e.g. camera 104, video display 106, speaker 108, one-touch call button 110, microphone 112, keypad 120, etc.). The communication housing 102 may be made of a material, including but not limited to polymer (for example, polyvinyl chloride, polystyrene and the like) or metal. The communication housing 102 may include a base (not shown). The base may rest on a countertop or other substantially horizontal surface. The communication housing 102 may be a solid structure with a hollow center portion. Components may be arranged on, or at least partially in, the communication housing 102 so as to be accessible to a dependent or caretaker. In certain examples, portions of components may protrude through openings in the solid walls of the communication housing 102 to make them accessible to a dependent or caretaker.

Certain embodiments may comprise web link circuitry (not shown). In certain examples, the camera 104, video display 106, speaker 108, one-touch call button 110, microphone 112, audio amplifier (not shown), medication door 116, and mass-sensing receptacle 118 may be electrically coupled or otherwise interconnected via the web link circuitry. In certain examples, the web link circuitry may be operable to communicate with a remote device (e.g. smartphone, computer, and the like). The web link circuitry may be coupled to a caregiver's phone or computer through 3G, 4G, wireless, wired, telephonic, or other means of electrical signal transmission. The web link circuitry may be contained, at least partially, in the communication housing 102.

In certain examples, the web link circuitry may be programmed using the keypad 120. In certain embodiments, the web link circuitry may be contained at least partially within the communication housing 102. Web link circuitry may be configured so as to permit communication between a caretaker and a dependent. In certain examples, web link circuitry may be configured to transmit data from the camera 104 and microphone 112 to a caretaker's smartphone, and receive data from the caretaker's smartphone and transmit the data from the smartphone to the video display 106, speaker 108, or medication management assembly 114. In certain examples, web link circuitry may be configured to allow only authorized users to establish communication using the apparatus 100.

Camera 104 is operable to capture video of a dependent. Camera 104 may be coupled to web link circuitry (not shown) such that the web link circuitry may transmit video from the camera 104 to a caretaker. In certain examples, camera 104 is a wide-angle web camera. In certain examples, the camera 104 may be disposed on or at least partially in, the communication housing 102. The camera 104 may be coupled to web link circuitry so as to allow a remote caretaker to view a dependent. An example camera 104 may be turned on or off using web link circuitry. Video data from the camera 104 may be sent to the caretaker, for example, via the web link circuitry. In some embodiments, the camera 104 may be arranged on, or at least partially in, the communication housing 102 such that the camera 104 collects image data corresponding to images of the dependent. In certain examples, the camera lens of camera 104 may face approximately horizontally relative to a surface on which the apparatus 100 set. In other examples, the camera lens of camera 104 may face a direction that is angled up or down relative to a plane of a surface on which the apparatus 100 sets. The camera 104 may be electrically coupled to the web link circuitry. The camera 104 may be configured to capture images and transmit the images to the web link circuitry. The camera 104 may be configured to receive images from the web link circuitry 102 and transmit the images to a caregiver.

An example apparatus may include a video display 106. The video display 106 is operable to display video of a caretaker to a dependent. The video display 106 may be sufficiently big such that dependents with poor eyesight can see the caretaker on the screen without straining their eyes. The video display 106 may be arranged on, or at least partially in, the communication housing 102. The video display 106 may be electrically coupled to the web link circuitry. In certain examples, if a call is initiated between a caretaker and a dependent, the video display 106 may show an image from a camera near a caretaker. For example, where a caretaker initiates a call from a smartphone with a video camera, the caretaker's smartphone may send the image of the caretaker to the dependent. The image of the caretaker may be sent either directly, such as through the web link circuitry, or through an intermediate. In certain examples, the video display 106 may also be used to show other images at the discretion of the caretaker, such as images of medications or reminders. The web link circuitry may be configured to transmit images to the video display 106, and the video display 106 may be configured to display the images received from the web link circuitry.

An example apparatus 100 may comprise at least one speaker 108. The speaker 108, or speakers, may be arranged on or at least partially in the communication housing 102, such that audio from the caretaker may be broadcast to the dependent. The speaker 108 may be coupled to an audio amplifier that is operable to amplify audio signals from the caretaker. Audio data from a caretaker may be transmitted from the caretaker's phone or computer to the web link circuitry, optionally through the audio amplifier, to the speaker 108. Optionally, the volume of the audio transmitted by the speaker 108 may be adjusted using the keypad 120. Optionally, the volume of the audio transmitted by speaker 108 may be adjusted using a volume knob, such as a rotary dial (not shown).

An example apparatus may include a one-touch call button 110. The one-touch call button 110 may allow a dependent to easily initiate contact with another person, such as a caretaker. The one-touch call button 110 may be arranged, for example, on, or at least partially in, the communication housing 102. In an example device, by pressing the one-touch call button 110 a call may be initiated to a caretaker's phone or emergency services. In certain examples, the entity that is called when the one-touch call button 110 is depressed is programmable through the keypad 120. The one-touch call button 110 may be electrically coupled to the web link circuitry. The web link circuitry may be configured to make a phone call to a caregiver (e.g. a call is made to a caregiver's smartphone) at or around the time the one-touch call button 110 is pressed.

An example apparatus 100 may comprise a microphone 112. In certain examples, the microphone 112 may be electrically coupled to the web link circuity. The microphone 112 may be arranged on, or at least partially in, the communication housing 102, such that audio from the dependent may be captured by the microphone 112 and transmitted to the caretaker through web link circuitry. In certain examples, the microphone 112 may be configured such that when a computer control mechanism activates the apparatus 100 and a call is initiated between the caretaker and dependent, the microphone 112 transmits audio signals to a remote device through the web link circuitry. The microphone 112 may be configured to capture audio input and transmit the input to the web link circuitry. The web link circuitry may be configured to receive audio input from the microphone 112 and transmit the audio input to a caregiver.

An example apparatus may comprise a keypad 120. The keypad 120 may be a touch-screen, an array of buttons, or any other type of keypad operable to electrically communicate with components of the apparatus. In certain examples, the keypad 120 may be operable to allow a user to program who is called when the one-touch call 110 button is pressed. In certain examples, the keypad 120 may be operable to allow a dependent to send text messages, and other message types, to a caretaker. In certain examples, the keypad 120 may be operable to allow a dependent to adjust the volume of audio produced by speaker 108. In certain examples the keypad 120 may facilitate the programming of 3G, 4G, and web access connectivity of the apparatus 100.

An example device may optionally comprise a medication management assembly 114. In certain examples, the medication management assembly 114 may include its own housing, such as is shown in FIG. 1. In other examples, the components of the medication management assembly 114 (e.g. medication door 116, mass-sensing receptacle 118, medication chute 204, or medication cartridge assembly 202) may be on, or at least partially in, the communication housing 102. Optionally, a communication housing 102 and a medication management assembly 114 may be designed to couple or interlock with each other. An example of a medication management assembly 114 comprises medication cartridge assembly 202, a medication chute 204, and a medication door 116. An example medication management assembly may optionally comprise a mass-sensing receptacle 118.

The medication door 116 may optionally be arranged on the surface of, or at least partially in, the medication management assembly 114, such that medication will travel down the medication chute 204 and through the medication door 116. The medication door 116 may be either powered to open when the medication cartridge assembly 202 is activated by the web link circuitry, or it may be passive and open with the force of falling medication. The medication door 116 may be disposed between a medication chute 204 and a mass-sensing receptacle 118.

An example apparatus 100 may include an optional mass-sensing receptacle 118. In certain examples, the mass-sensing receptacle 118 may be arranged underneath the medication door 116. In certain examples the mass-sensing receptacle 118 may be disposed at the bottom of the medication chute 204, such that solid form medication falls through the medication door 116 and into the mass-sensing receptacle 118. The mass-sensing receptacle 118 may be electrically coupled to the web link circuitry so that a caregiver can determine whether the medication management assembly 114 has dispensed the appropriate quantity of medication. The mass-sensing receptacle 118 may be configured to transmit data to web link circuitry and the web link circuitry may transmit the data such that a caregiver can remotely determine how much mass remains in the mass-sensing receptacle 118. The mass-sensing receptacle 118 may be configured to transmit data corresponding to the mass of objects (e.g. medication) in the mass-sensing receptacle 118. The data corresponding to the mass of objects in the mass-sensing receptacle 118 may be transmitted to a caregiver via web link circuitry. In certain examples, the mass-sensing receptacle 118 is shaped like a cup, bowl, or dish.

A medication cartridge assembly 202 (see FIG. 2) is operable to release medication for consumption by a dependent. The medication cartridge assembly 202 may be any medication cartridge assembly capable of remote activation. In certain examples, the medication cartridge assembly 202 may be remotely activated by a caretaker. In certain examples, the medication cartridge assembly 202 may be electrically coupled to the web link circuitry. In certain examples, the medication cartridge assembly 202 may be activated using web link circuitry.

An optional medication chute 204 may be arranged on, or at least partially in, the medication management assembly 114, such that medications that are released by the medication cartridge assembly 202 travels down the medication chute 204 towards the medication door 116.

Certain examples may facilitate the managing of a dependent's medication. In certain examples, a video phone may optionally be electrically or physically coupled to a medication management assembly 114. In some embodiments, the medication management assembly 114 may be electrically connected to web link circuitry. In certain examples, the medication management assembly 114 can disburse medication, either automatically, on demand by a dependent, or remotely by, for example, a caretaker.

Figure 2:
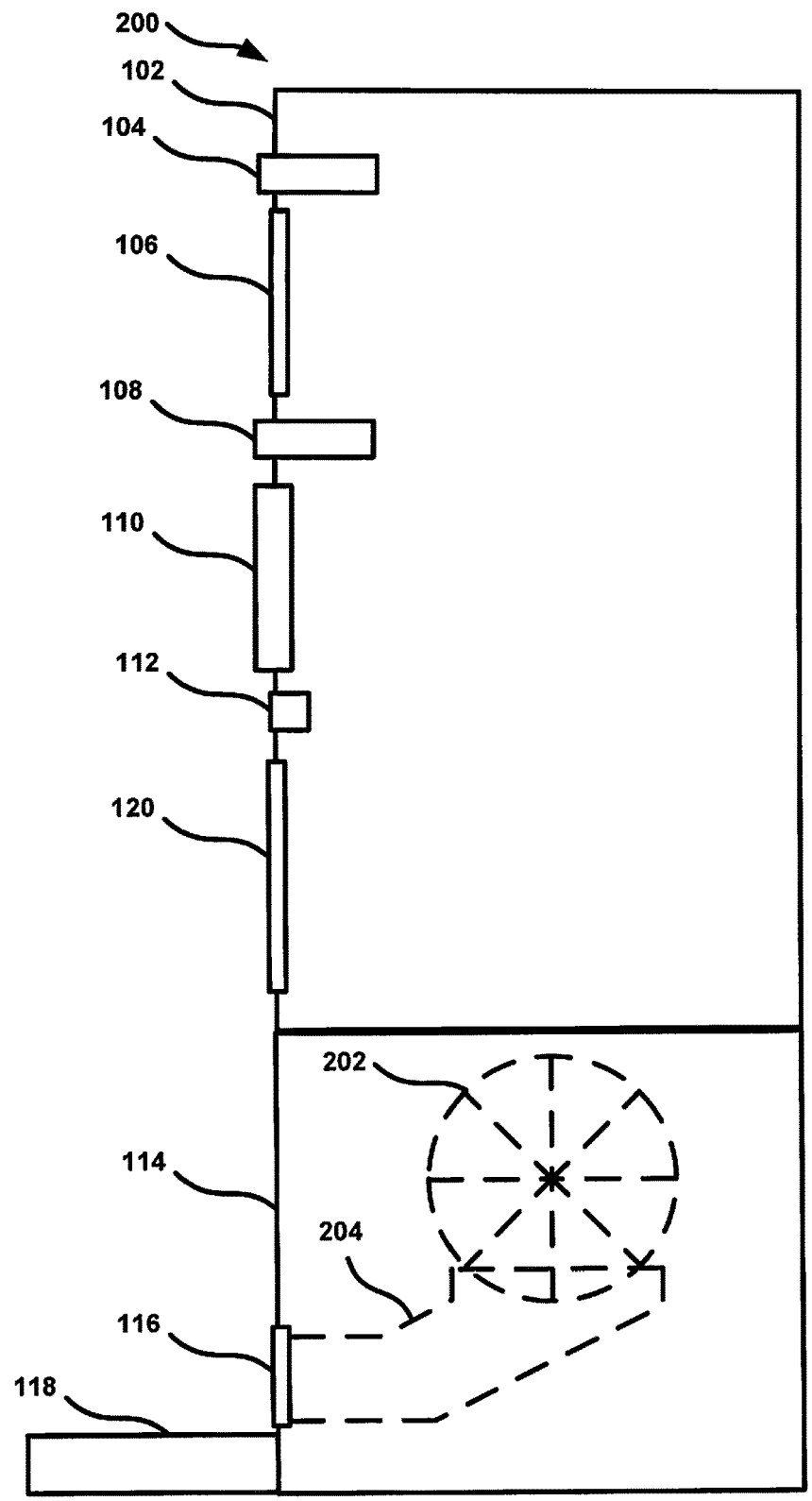
FIG. 2 is a side view illustration of an apparatus according to an example embodiment.

FIG. 2 is a side-view illustration of an apparatus 200 according to an example embodiment. The apparatus 200 of FIG. 2 may be substantially similar to the apparatus 100 illustrated in FIG. 1. The apparatus 200 may include components such as the camera 104, video display 106, speaker 108, one-touch call button 110, microphone 112, and optional keypad 120 arranged on or at least partially in, communication housing 102. The apparatus 200 components may be arranged on, or at least partially in, the communication housing 102 such that a dependent can easily use apparatus 200 to communicate with a caretaker. In certain examples, the apparatus 200 may further include a medication management assembly 114. The medication management assembly 114 may include components such as the medication door 116, mass-sensing receptacle 118, medication cartridge assembly 202, and medication chute 204. The components of the apparatus 200 may be substantially similar to those components described in FIG. 1.

A caretaker's phone number may be either a traditional phone line number, or it may be a VOIP number or IP address, or it may be any other address that permits communication. For example, entering the caregiver's phone number into the keypad 120 may result in establishing a connection to a smart phone, land-line phone, a laptop computer, a desktop computer, or a tablet.

Some examples of the apparatus 200 may include a medallion. The medallion may be used to facilitate communication. For example the medallion may be used to create a connection between a dependent and a caretaker or to emergency services. In certain embodiments, a medallion may allow a dependent to quickly request assistance. The request for assistance may transmit a message to a caretaker or emergency services without requiring a dependent to have close access to a phone or access to the apparatus. In some embodiments, a medallion may be carried with the dependent, such as on a necklace. The medallion may be electrically coupled to the web link circuitry. In certain examples, the medallion may be configured to send an emergency signal directly to a caretaker or emergency services or other remote parties.

Embodiments of the invention may incorporate software which is password protected, such that a caretaker's authorization must be established before audio or visual communication or medication management system control is established. Authorized users of the device may include caretakers, dependents, or other entities, such as medical professionals, who possess the valid authentication key for the device.

Figure 3:
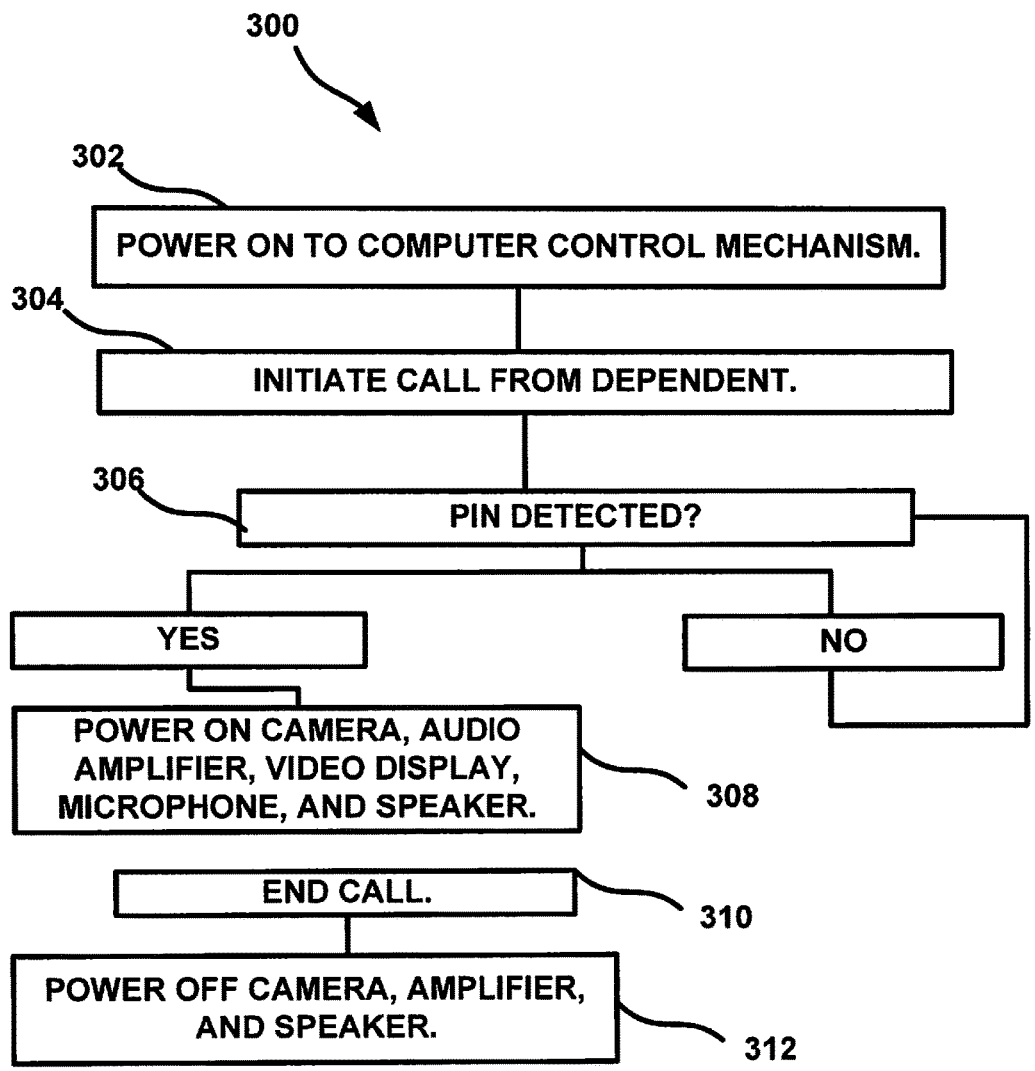
FIG. 3 is a method of contacting a caregiver according to an example embodiment.

FIG. 3 depicts a method 300 of establishing and terminating communication between a caretaker and dependent, according to an example embodiment. The method may include supplying power to a computer control mechanism 302. The power to the computer control mechanism may be continuous and substantially uninterrupted so as to allow a dependent to utilize the corresponding apparatus at virtually any time. The computer control mechanism may be a microcontroller, processor, motherboard, or any other component capable of controlling electrical signals in example embodiments. A call may be initiated between a caretaker and a dependent 304. In some examples, the call may be initiated some time after the dependent presses the one-touch call button 110 or a button on a medallion. In other examples, the call may be initiated some time after the caretaker dials the phone number of the dependent or optionally, the computer control mechanism may establish a connection to web link circuitry. The computer control mechanism or web link circuitry waits for a valid personal identification number (PIN), password, or other valid authentication key 306. The PIN, password, or other valid authentication key may be programmed into the device using the keypad 120. In certain examples if no PIN is detected or if an invalid PIN is detected the computer control mechanism or web link circuitry may wait for a valid PIN. In certain examples, if an invalid PIN, password, or other authentication key is detected the computer control mechanism may disconnect from the web link circuitry or the computer control mechanism may provide another opportunity to enter a valid PIN, password, or authentication key. If a valid authentication key is detected then power is supplied to the camera 104, video display 106, microphone 112, optionally to the optional audio amplifier, and optionally to the speaker 108 (if the speaker requires power) 308. At this point the dependent has established a telephonic connection. The call is ended after the reason for the call is resolved or remains unresolved 310. The call may be ended by the dependent, such as by pressing the one-touch call button 110 or powering off the apparatus. Alternatively, the call may be ended by the entity who received the call, such as a caretaker. Power to the camera 104, the audio amplifier, video display 106, microphone 112, and the speaker 108 is turned off 312.

Figure 4:
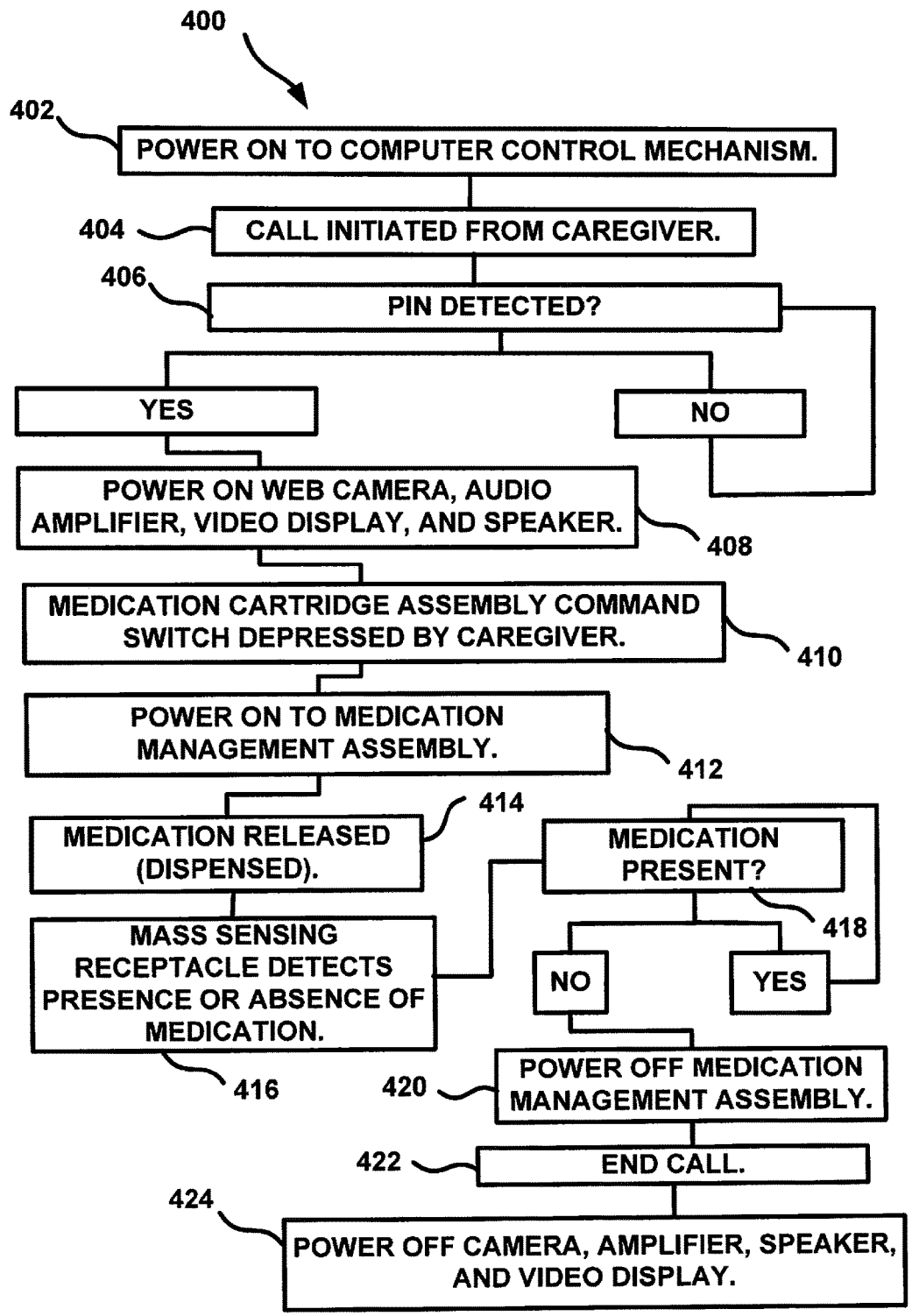
FIG. 4 is a method of remotely dispensing medication according to an example embodiment.

FIG. 4 illustrates a method 400 of remotely dispensing medication according to an example embodiment. In certain examples, the medication may be dispensed remotely through a remote caregiver. Power may be supplied to a computer control mechanism 402. The power to the computer control mechanism may be continuous and substantially uninterrupted so as to allow a dependent to utilize the apparatus at virtually any time. The computer control mechanism may be a microcontroller, processor, motherboard, or any other component capable of controlling electrical signals in example embodiments. A call may be initiated from a caregiver 404. The caregiver may initiate the phone call using a web application, by dialing the phone number of the dependent, or by other means of communicating with an example apparatus. Optionally, the computer control mechanism may establish a connection to web link circuitry. At this point, in order to gain access to the apparatus the caregiver may be required to supply a sufficient PIN, password, or other authentication key. The computer control mechanism or web link circuitry may detect whether a valid PIN, password, or authentication key is presented 406. The PIN, password, or other valid authentication key may be programmed into the device using the keypad 120. In certain examples if no PIN is detected or if an invalid PIN is detected the computer control mechanism or web link circuitry may wait for a valid authentication key. In certain examples, if an invalid PIN, password, or other authentication key is detected the computer control mechanism may disconnect from the web link circuitry or the computer control mechanism may provide another opportunity to enter a valid PIN, password, or authentication key. If a valid authentication key is detected then power is supplied to the camera 104, video display 106, microphone 112, optionally to the optional audio amplifier, and optionally to the speaker 108 (if the speaker requires power) 408. In certain examples, the caregiver may control at least one medication cartridge assembly command switch. A caregiver may press the at least one medication management assembly command switch 410. A medication management assembly command switch may command a medication assembly to power on, power off, or dispense medication. The medication management assembly command switch may be, for example, a number on a phone dial pad which has been pre-programmed to initiate medication release. Power is supplied 412 to the medication cartridge assembly 202. Medication may be released 414. The medication may be released from a medication cartridge assembly 202 into a medication chute 204. The medication chute 204 may direct the medication through a medication door 116 and into a mass-sensing receptacle 118. The mass-sensing receptacle 118 may detect the amount of mass present 416 in the mass-sensing receptacle 118. The mass-sensing receptacle 118 may indicate, through the web link circuitry, whether mass is still present 418 in the mass-sensing receptacle 118. When there is no longer mass present in the mass-sensing receptacle 118 and the dependent has ingested the medication, the medication cartridge assembly 202 is powered off 420. The call may be ended 422. The audiovisual components, such as the camera 104, audio amplifier, microphone 112, speaker 108, and video display 106 may be turned off 424.

The preceding description has been presented only to illustrate and describe example embodiments of the disclosure. It is not intended to be exhaustive or to limit the disclosure to any precise form disclosed. Many modifications, combinations and variations are possible in light of the above teachings. Although specific examples have been illustrated and described herein, it will be appreciated by those of ordinary skill in the art that any arrangement calculated to achieve the same purpose could be substituted for the specific examples shown. This application is intended to cover adaptations or variations of the present subject matter. Therefore, it is intended that the disclosure be defined by the attached claims and their legal equivalents.

What is claimed is:

1. An apparatus for audiovisual communication between a caregiver and a dependent while dispensing a medication, comprising:
    web link circuitry configured to communicate with a remote caregiver device;
    a medication cartridge assembly electrically coupled to the web link circuitry;
    a mass-sensing receptacle electrically coupled to the web link circuitry and configured to transmit the mass of any medication in the mass-sensing receptacle to the web link circuitry;
    a camera electrically coupled to said web link circuitry and configured to capture images of said dependent and transmit said images to said web link circuitry, and said web link circuitry configured to receive said images from said camera and transmit said images to said caregiver; and
    a microphone electrically coupled to the web link circuitry and configured to capture audio input and transmit the audio input to the web link circuitry, and the web link circuitry configured to receive the audio input and transmit the audio input to a caregiver;
    said camera and microphone powered on responsive to said communication between said web link circuitry and said remote caregiver device to establish said audiovisual communication between said caregiver and said dependent;
    said medication cartridge assembly powered on during said audiovisual communication between said caregiver and said dependent and configured to dispense medication responsive thereto; and
    said medication cartridge assembly powered off during said audiovisual communication between said caregiver and said dependent responsive to said mass-sensing receptacle detecting a presence of mass in said mass-sensing receptacle followed by an absence of mass in said mass-sensing receptacle.

2. The apparatus of claim 1, further comprising a housing adapted to accommodate the web link circuitry.

3. The apparatus of claim 1, wherein said medication cartridge assembly is powered on responsive to a medication management assembly command switch being pressed during said audiovisual communication between said caregiver and said dependent.

4. The apparatus of claim 1, further comprising a video display,
    the video display electrically coupled to the web link circuitry,
    the web link circuitry configured to transmit images to the video display, and
    the video display configured to display images received from the web link circuitry.

5. The apparatus of claim 1, wherein said mass-sensing receptacle transmits an amount of mass in said mass-sensing receptacle to said caregiver.

6. The apparatus of claim 1, further comprising a one-touch call button,
    the one-touch call button electrically coupled to the web link circuitry, and
    the web link circuitry configured to make a phone call to a caregiver at or around the time the one-touch call button is pressed.

7. The apparatus of claim 1, wherein the web link circuitry is configured to allow only authorized users to establish communication with the dependent.

8. The apparatus of claim 1, further comprising a medication chute,
    the medication chute disposed such that objects dispensed by the medication cartridge assembly travel through the medication chute.

9. The apparatus of claim 8, further comprising a medication door,
    the medication door disposed between the medication chute and the mass-sensing receptacle.

10. A method of remote audiovisual provision of medication to a dependent, the method comprising the steps of:
    electrically coupling a camera configured to capture images of said dependent and a microphone configured to capture audio input from said dependent with a caregiver device remote from said dependent to operably audiovisually communicate with said remote caregiver device;
    powering on said camera and microphone to establish said audiovisual communication between said caregiver and said dependent;
    activating a medication cartridge assembly subsequent to said powering on step and during said audiovisual communication between said caregiver and said dependent and thereby causing said medication cartridge assembly to dispense medication;

detecting a presence of said medication in a mass-sensing receptacle subsequent to said activating step;

determining an absence of said medication in said mass-sensing receptacle subsequent to said detecting step;

deactivating said medication cartridge assembly during said audiovisual communication between said caregiver and said dependent and subsequent to said determining step; and powering off said camera and microphone to disconnect said audiovisual communication between said caregiver and said dependent subsequent to said deactivating step.

11. The method of claim 10, wherein said step of electrically coupling a camera and a microphone with a caregiver device remote from said dependent further comprises electrically coupling web link circuitry to said camera, said microphone, and said remote caregiver device.

12. The method of claim 11, further comprising the step of electrically coupling said web link circuitry with a mass-sensing medication receptacle, said mass-sensing medication receptacle operable to detect if a mass is present in said mass-sensing medication receptacle and to transmit said mass present in said mass-sensing medication receptacle to said web link circuitry.

13. The method of claim 11, further comprising the steps of:

electrically coupling a video display to the web link circuitry, transmitting images from said web link circuitry to the video display, and displaying the images received from the web link circuitry on the video display.

14. The method of claim 11, wherein said step of powering on said camera and microphone to establish said audiovisual communication between said caregiver and said dependent is responsive to a communication between said web link circuitry and said remote caregiver device.

15. The method of claim 14, further comprising the steps of:

electrically coupling a one-touch call button to the web link circuitry, pressing said one-touch call button; and establishing said audiovisual communication between said caregiver and said dependent through the web link circuitry responsive to said pressing step.

16. The method of claim 11, wherein the web link circuitry is configured to allow only authorized users to establish communication with the apparatus.

17. The method of claim 11, further comprising the step of transmitting an amount of mass in said mass-sensing receptacle to said caregiver.

18. The method of claim 10, wherein said medication cartridge assembly is activated responsive to a medication management assembly command switch being pressed during said audiovisual communication between said caregiver and said dependent.

* * * * *